United States Patent [19]

Stouffer et al.

[11] 4,122,845

[45] Oct. 31, 1978

[54] PERSONAL CARE SPRAY DEVICE

[75] Inventors: Ronald D. Stouffer, Silver Spring; Harry C. Bray, Jr., Beltsville, both of Md.

[73] Assignee: Bowles Fluidics Corporation, Silver Spring, Md.

[21] Appl. No.: 818,215

[22] Filed: Jul. 22, 1977

Related U.S. Application Data

[60] Division of Ser. No. 618,208, Sep. 30, 1975, Pat. No. 4,052,002, which is a continuation of Ser. No. 510,722, Sep. 30, 1974, abandoned.

[51] Int. Cl.² .............................................. A61H 9/00
[52] U.S. Cl. ........................................ 128/66; 401/15; 401/137; 239/102
[58] Field of Search ................... 401/288, 286, 289; 239/101, 102, 588, 288.5; 15/110; 128/66; 137/826, 835

[56] References Cited

U.S. PATENT DOCUMENTS

| Re. 27,938 | 3/1974 | Bauer | 239/102 |
|---|---|---|---|
| 785,824 | 3/1905 | Nicholls | 401/28 |
| 3,283,352 | 11/1966 | Yow-Jiun Hu | 128/65 |
| 3,507,275 | 4/1970 | Walker | 128/66 X |
| 3,910,265 | 10/1975 | Coleman | 128/66 |
| 3,973,558 | 8/1976 | Stouffer et al. | 128/66 |
| 4,052,002 | 10/1977 | Stouffer et al. | 239/102 X |

*Primary Examiner*—John J. Love
*Attorney, Agent, or Firm*—Rose & Edell

[57] ABSTRACT

A personal care spray device, particularly suitable for use as a facial cleanser and massager, is connected to a faucet and issues a cyclically swept liquid jet against the user's body. A guard wall surrounds the jet outlet opening to prevent splashing and serve a wiping function.

5 Claims, 26 Drawing Figures

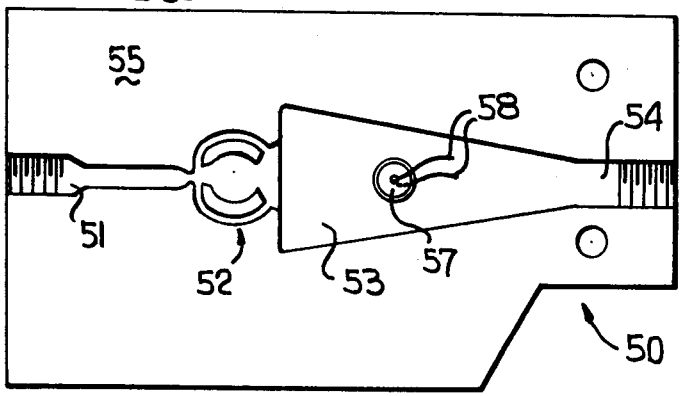
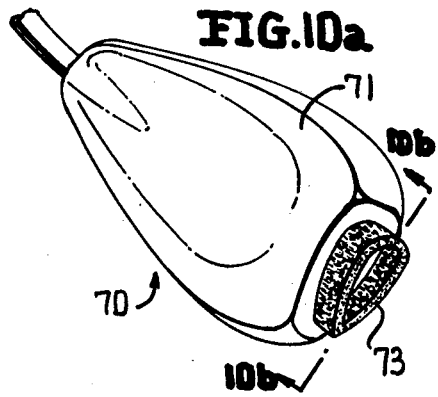
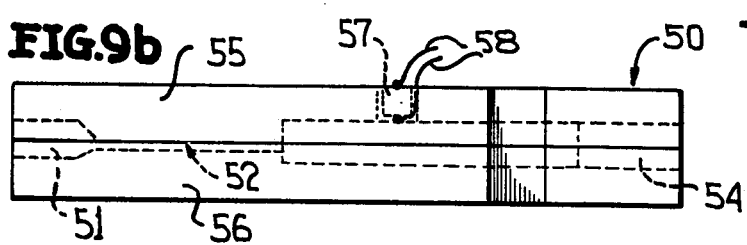
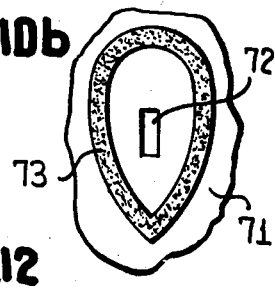
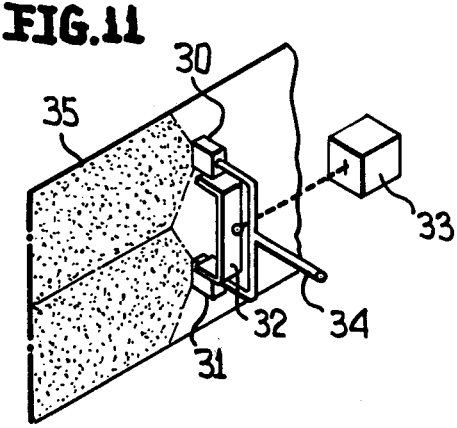
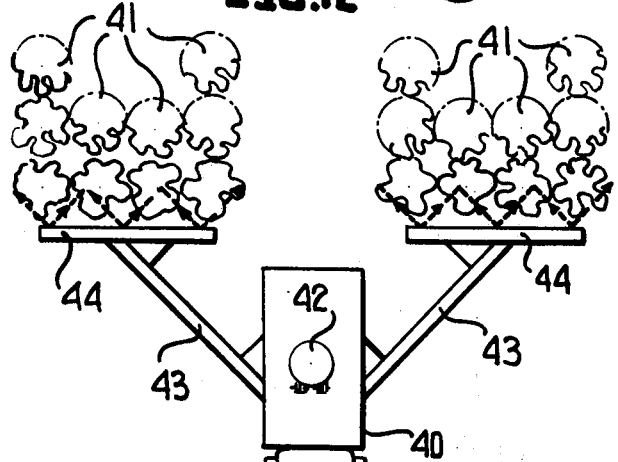
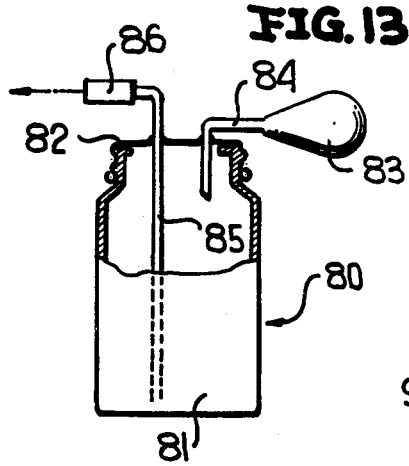
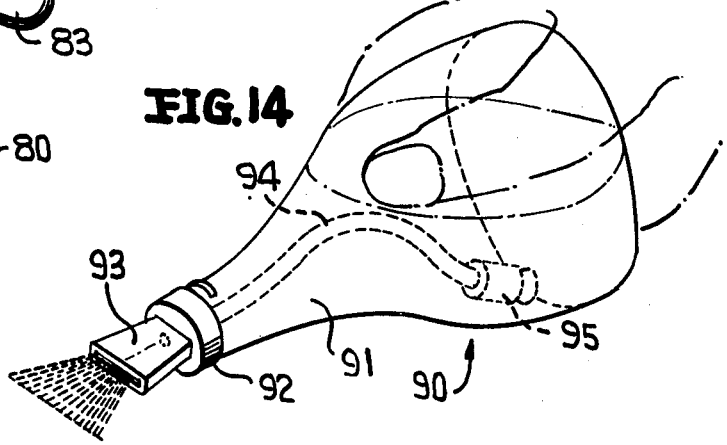

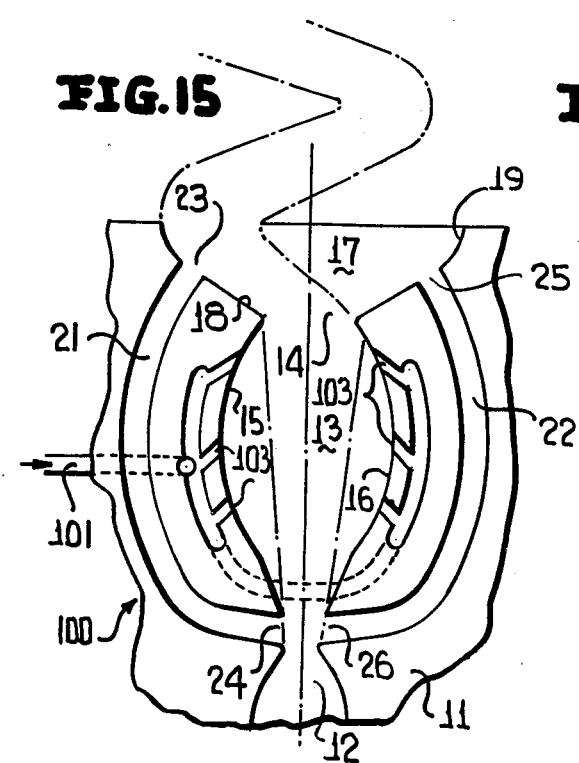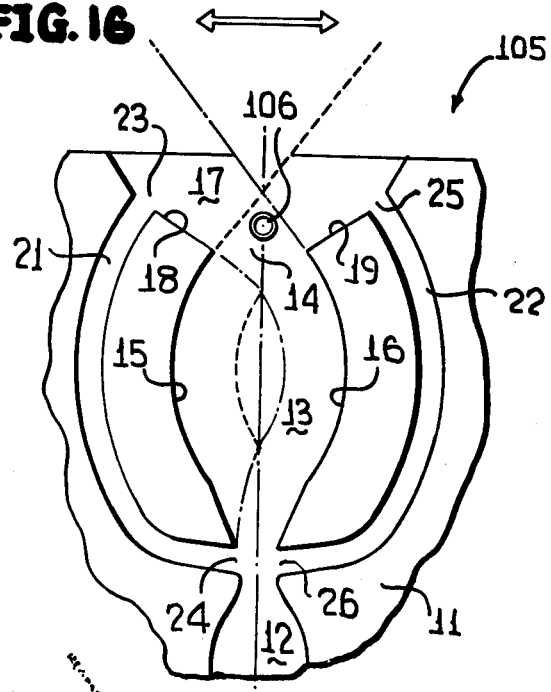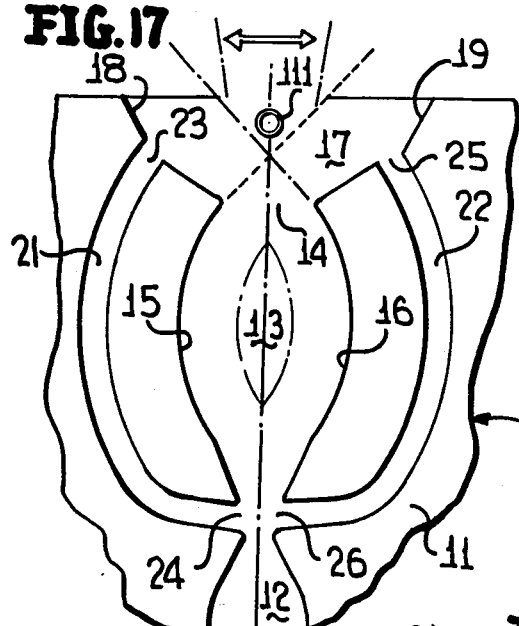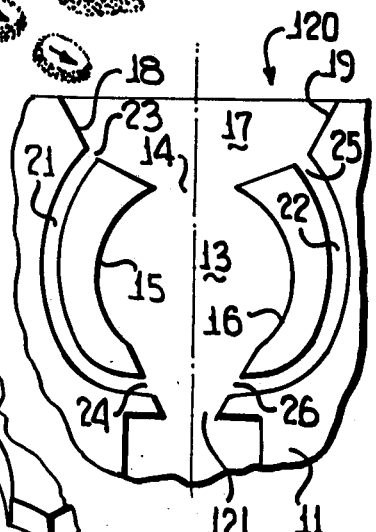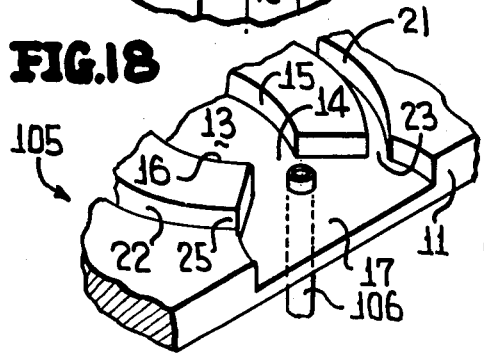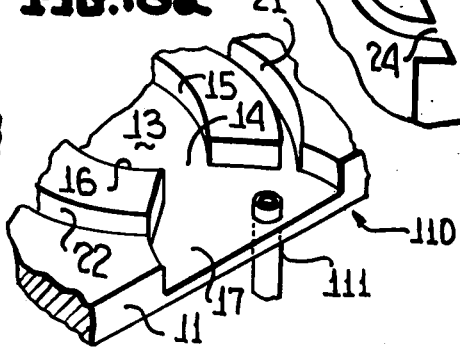

PERSONAL CARE SPRAY DEVICE

This is a division, of application Ser. No. 618,208, filed Sept. 30, 1975, now U.S. Pat. No. 4,052,002, which is a continuation of Appln. Ser. No. 510,722, filed 9/30/74, now abandoned.

BACKGROUND OF THE INVENTION

The present invention relates to method and apparatus for effecting controlled dispersal of fluid. More particularly, the present invention relates to techniques for cyclically deflecting a fluid jet in order to achieve specific flow patterns at significantly lower pressures than possible with prior art techniques. Although the initial discussion hereinbelow relates specifically to liquid spray techniques, it will be apparent that the inventive concepts described herein are applicable also to the dispersal of other fluids, including gas, fluidized solid particles, etc.

Commercial and industrial liquid spray apparatus have heretofore utilized the so-called shear nozzle, which is a sharpedged orifice with an outlet shaped to provide a desired spray pattern. Characteristically, a given size shear nozzle issues liquid in droplet form and in a defined spray pattern, with both droplet size and pattern configuration being dependent in part on the pressure of the liquid applied to the nozzle. Specifically, droplet size varies inversely with pressure, the rate of change being relatively small. The spray pattern, on the other hand, remains constant over a large range of pressures above a predetermined pressure, but the pattern degrades significantly at lower pressures. The pressure required to achieve a specific droplet size is also affected by the surface tension of the liquid, with a liquid of higher viscosity requiring a higher pressure than a liquid of lower viscosity to achieve reduction to a given droplet size. Likewise, the predetermined pressure above which the shear nozzle issues a constant or nondegraded spray pattern is affected by viscosity, the higher the viscosity the higher the predetermined pressure.

Different liquid spray applications have different requirements with respect to droplet size and spray pattern. For example, in the field of liquid paint spraying it is important that the droplets be sufficiently small so as not to form globules on the painted surface, generally on the order of 25 microns or less. In addition, it is important that the paint spray pattern configuration be predictable. Therefore, shear nozzles employed in paint spray applications must be operated at pressures above that which provides the maximum permissible droplet size and in the pressure range over which the spray pattern remains constant. Generally, this pressure range is higher than the pressure required to achieve the sufficiently small droplets. In comparison, agricultural sprays (i.e. pesticides, fertilizers, etc.) require that the droplet size be larger than approximately 80 microns because smaller droplets are readily carried away by air currents and thereby create pollution hazards and waste. In addition, spray pattern uniformity (i.e. uniform distribution of liquid throughout the spray pattern) is important in many agricultural spray applications. Thus, agricultural spray applications employ lower flow velocities than paint sprays. Consequently, shear nozzles for agricultural spray use are operated at pressures on the order of 50 psi to achieve the desired spray pattern whereas paint spray shear nozzles are typically operated at pressures on the order of a few thousand psi. In each industry, with cost reduction as an ultimate goal, there has been many attempts to reduce the required operating pressures without sacrificing the respective droplet and spray pattern characteristics. Thus far these attempts have been unsuccessful.

It is therefore an object of the present invention to provide a method and apparatus for achieving a predictable liquid spray pattern with controlled droplet sizes at liquid operating pressures which are significantly lower than are possible with prior art methods and apparatus.

It is another object of the present invention to provide a method and apparatus for achieving a predictable liquid spray pattern, wherein substantially all droplets are below a specified size, at operating pressures well below those which are required in the prior art.

It is another object of the present invention to provide a method and apparatus for achieving a predictable liquid spray pattern, wherein substantially all droplets are above a specified size, at operating pressures well below those required in the prior art.

It is yet another object of the present invention to provide a capability for issuing a liquid spray pattern wherein liquid is uniformly distributed over the pattern and wherein substantially all of the droplets are of uniform size.

Experiments by Rayleigh and others have indicated that if an orifice is vibrated transversely of its flow axis above is specific amplitude and frequency, a liquid jet issued from that orifice breaks up into droplets of controlled periodicity and spacing. Generally, the amplitude of the vibratory translation must be at least equal to the radius of the orifice; the frequency must be equal to or greater than what shall be termed the Rayleigh frequency which is inversely related to the orifice diameter and directly related to the surface tension of the liquid. It would seem therefore, that an orifice could be vibrated transversely of its flow axis at sufficient amplitude and frequency to achieve controlled droplet formation, and at the amplitude necessary to achieve the desired spray pattern configuration. Theoretically, this is possible; but as a practical matter, achieving the vibration amplitude required for the desired spray pattern configuration at frequencies equal to or greater than the Rayleigh frequency requires a driven mechanism which of itself is more complex and expensive and requires more energy to operate than would justify changeover from the shear nozzle approach.

It is also known that liquid jets can be transversely deflected without the need for external energy sources. For example, a member in which an orifice or nozzle is defined may be reciprocated or vibrated by the energy of the operating fluid to be issued by the orifice. Typically, the reciprocating drive member would be a turbine which is driven by the liquid flowing past the turbine blades to the orifice. This approach, although not requiring any external energy, requires relatively high operating pressures to achieve the necessary reciprocation amplitude at frequencies as high or higher than the Rayleigh frequency. In addition, the fast moving mechanical components of the reciprocating mechanism are subject to failure due to constant wear and tear.

Fluidic oscillators are well known in the prior art and are widely used in many applications requiring a cyclically deflected fluid jet. Examples of fluidic oscillators may be found in U.S. Pat. Nos. 3,016,066 (Warren), 3,185,166 (Horton et al), 3,247,861 (Bauer), 3,432,102 (Turner et al), and 3,563,462 (Bauer). Operation of all fluidic oscillators is characterized by the cyclic deflection of a fluid jet without the use of mechanical moving parts; consequently, fluidic oscillators are not subject to the wear and tear which adversely affects the reliability and operation of pneumatic oscillators and reciprocating nozzles. Furthermore, since only the jet and not the entire orifice-bearing body is translated, much less energy is required to achieve jet oscillation.

The oscillators described in the aforementioned Warren and Horton et al patents are characterized by their use of boundary layer attachment (i.e. Coanda effect). Specifically, these oscillators include an interaction region with sidewalls which diverge downstream from a power nozzle. A jet issued by the power nozzle is cyclically deflected back and forth between the interaction region sidewalls, either by a portion of the jet which is fed back to effect deflection or by some other feedback force generated when the jet attaches to a sidewall. The feedback force must not only be sufficient to deflect the jet itself, but it must also overcome the boundary layer attachment of the jet to a sidewall. The result is that the oscillator cannot operate at jet pressures below a rather significant pressure level. Moreover, the attachment of the jet to the sidewalls during each half cycle of oscillation results in a "dwell" time wherein the jet is stationary. The spray pattern produced by the cyclically deflected jet contains greater concentrations of jet fluid at pattern locations corresponding to a stationary jet than at other locations. It is therefore not possible to control pattern distribution or to achieve uniformly distributed patterns, with oscillators of this type.

The oscillators described in the Turner et al and Bauer patents are characterized by what is sometimes called a flow-reversing interaction region. The sidewalls of the flow-reversing interaction region first diverge from the power nozzle and then converge toward an outlet throat in a downstream direction. When the jet flows along the left sidewall it is re-directed thereby toward the right as it egresses through the outlet throat; likewise, the right sidewall re-directs the jet toward the left. The entry of ambient fluid into the interaction region via the outlet throat is relatively restricted as compared to the Horton et al or Warren oscillators, primarily because the outlet throat is narrower relative to the egressing jet than the downstream end of the Horton et al and Warren oscillators. The limitation of ambient fluid entry reduces the boundary layer attachment to the interaction region sidewalls so that less feedback force is required to deflect the jet. Oscillation in the flow-reversing configuration is therefore possible at lower jet pressures than in the Horton et al and Warren oscillators. Because of this and other practical considerations oscillators with flow-reversing interaction regions have found numerous practical applications, such as in shower heads, lawn sprinklers, decorative fountains, industrial control equipments, etc. Nevertheless, prior art fluidic oscillators are not suitable for spray applications described supra. This is primarily due to the fact that in prior art fluidic oscillators, substantial amounts of ambient fluid or re-circulated jet fluid is ingested into the interaction region. In the Horton et al and Warren oscillators, ambient fluid enters the interaction region through the downstream end thereof and through the control passages. In the Horton et al oscillator a portion of the jet is also fed back into the interaction region. In the Bauer and Turner et al oscillators, both ambient fluid and re-circulated jet fluid are fed back into the interaction region through feedback passages. The ingestion of ambient or re-circulated jet fluid into the interaction region is undesirable for many reasons. Specifically, many spray applications require that the jet fluid not be contaminated with ambient fluid, or with jet fluid inter-mixed with ambient fluid, prior to issuance of the jet. For example, in paint spraying such ingestion tends to cause deposits of paint on the walls of the sprayer, resulting in clogging and eventual termination of flow.

Ingestion of air into the interaction region also adversely affects the spray pattern and droplet size of the liquid issued by a fluidic oscillator. Specifically, the spray pattern of liquid issued from a fluidic oscillator is generally fan-shaped. Within the fan configuration, it is desirable to provide as uniform a distribution of liquid as possible. If air is intermixed with the issued liquid, regions of air will be randomly interspersed in the fan-pattern, destroying the uniformity of liquid distribution in the pattern. In addition, the mixture of air and liquid has a different viscosity than the liquid alone, so that droplet size, which is a function of viscosity, is affected thereby.

In aerosol spray units, typically the freon or other propellant liquid is delivered from a nozzle mixed with the delivered fluid but retains its droplet form until it can explode in the ambient environment. Heretofore, fluidic elements were not practical for use with aerosol units because the low static pressure, relative to ambient, in the interaction region of the element, permitted the premature explosion of the freon droplets in the element. Similar rationale applies to the spray of fluid with a foamant-type additive; that is, premature foaming occurs in low-pressure interaction regions.

As previously mentioned, agricultural spraying applications require that droplets be larger than approximately 80 microns, a characteristic which cannot be readily achieved with prior art fluidic oscillators. Specifically, in prior art oscillators the sweeping liquid jet impinges on opposite walls of an outlet region such that the side of the jet experiences a shearing effect along the wall. The shearing in turn produces many extremely small droplets, called "fines", which are considerably smaller than the permissible droplet size.

Another disadvantage of prior art fluidic oscillators relates to their size. As indicated in the aforementioned U.S. Pat. No. 3,563,462 to Bauer, the flow reversing type oscillator of the prior art does not oscillate if the interaction region length is less than approximately nineteen times the power nozzle width, or if the outlet throat is less than twice the power nozzle width. Since the power nozzle width is often dictated by the desired characteristics for the issued spray, the minimum overall dimensions of the oscillator are likewise fixed, often at a size which is impractical for the application.

A further disadvantage of prior art fluidic oscillators relates to their minimum aspect ratio, defined as the ratio of the power nozzle depth to the power nozzle width. Generally, this ratio is on the order of two and in some applications, it may be as low as one, however; at lower aspect ratios prior art oscillators have been inoperable. As a practical matter, smaller aspect ratios permit simpler and less costly manufacturing processes to be employed in fabricating the oscillator. For example, aspect ratios on the order of 0.5 or less permit the use of single-sided etching, coining, and pantomilling techniques which are difficult, if not impossible to use in manufacturing small fluidic elements having larger aspect ratios. It is desirable, therefore, to employ the smallest aspect ratio possible without impairing oscillator operation.

In many spray and other flow applications it is desirable to monitor the flow rate of a fluid without actually sampling or otherwise disturbing the fluid flow. Preferably a flow monitor for achieving this result would operate irrespective of the compressibility of the working fluid. Ideally, such apparatus would provide an indication when a certain flow rate is achieved.

It is therefore one object of the present invention to provide an improved fluidic oscillator.

It is also an object of the present invention to provide a fluidic oscillator which operates without ingesting ambient fluid or re-circulated working fluid into the interaction region.

It is another object of the present invention to provide an improved fluidic oscillator of the type having a flow-reversing interaction region, the improvements permitting the oscillator to be constructed in much smaller size than prior art oscillators of this general type.

It is another object of the present invention to provide a fluidic oscillator capable of delivering liquid spray having a uniform spray pattern.

It is still another object of the present invention to provide a fluidic oscillator capable of delivering a liquid spray made up of droplet of uniform size.

It is yet another object of the present invention to provide an improved fluidic oscillator through which the flow rate can be monitored without employing flow or pressure sensors to disturb the flow.

It is another object of the present invention to provide a fluidic oscillator capable of operating with gaseous, liquid or fluidized solid working fluids in either a gaseous or liquid environment.

It is another object of the present invention to provide an improved fluidic oscillator capable of delivering a spray pattern of fluidized solid particles which are uniformly distributed for processing.

It is another object of the present invention to provide a personal massaging apparatus employing the fluidic oscillator.

It is still another object of the present invention to provide a paint spray apparatus employing a fluidic oscillator.

It is another object of the present invention to provide an agricultural spray apparatus employing a fluidic oscillator.

It is another object of the present invention to provide a portable personal spray apparatus employing the fluidic oscillator of the present invention.

SUMMARY OF THE INVENTION

In accordance with the principles of the present invention, a liquid jet is cyclically swept transversely of its flow direction, using only the energy in the applied pressurized liquid, in a manner such that the swept jet defines a prescribed flow pattern with controllable droplet size. In a preferred embodiment, the jet is issued from a fluidic oscillator of the type having flow-reversing interaction region sidewalls which first diverge from a power nozzle and then converge to an outlet throat. Two outlet walls diverge from the throat in a downstream direction to define an outlet region therebetween. The oscillator is characterized by the fact that, during operation, the static pressure at the upstream end of the interaction region is positive relative to the static pressure in the outlet region downstream of the outlet throat. Two oppositely-positioned control passages are provided, each communicating between the outlet region and the upstream end of the interaction region. The positive static pressure is developed by a combination of factors, including: a short interaction region length; and an outlet throat which is sufficiently narrow to permit the egressing jet to fully seal the interaction region relative to the outlet region.

A liquid jet issued from the power nozzle along the left sidewall of the interaction region is directed thereby through the outlet throat toward the right outlet wall. The positive static pressure at the upstream end of the interaction region, combined with the aspirating action of the jet proximate the right outlet wall, causes liquid to flow outwardly through right control passage to merge with the liquid jet. The positive static pressure at the upstream end of the interaction region is sufficient to maintain the left control passage filled with liquid. The outflow through the right control passage thus creates a lower pressure on the right side of the power jet at the upstream end of the interaction region, causing the jet to deflect toward the right sidewall of the interaction region. Flow and pressure conditions are thereby reversed, causing liquid to flow outwardly through the left control passage and to remain stationary in the right control passage. Oscillation ensues upon continuous reversal of flow conditions.

The merger of the control passage flow with the jet flow prevents the jet from being sheared by the outlet walls. Consequently, the "fines" or very small droplets resulting from such shearing are not produced. Moreover, the alternating of the control passages between outflow and liquid-full conditions assures that no fluid is ingested into the interaction region.

Liquid spray patterns issued by the oscillator are maintained integral (i.e. are not degraded) at far lower operating pressures than are required for shear nozzles. For example, in a test of a typical agricultural spray nozzle, it was found that the required fan-shaped pattern began to degrade at pressures below 30 psi and deteriorated completely below 15 psi. The oscillator described above, however, using the same liquid and configured to produce the same droplet size as the tested shear nozzle, retained an integral, non-degraded fan-shaped pattern at pressure as low as 0.75 psi. Similarly, in a test of a typical shear nozzle employed for paint spraying, it was found that an operating pressure on the order of a thousand psi was required to produce sufficiently small droplets and a pressure in excess of two thousand psi was required to achieve a non-degraded spray pattern; on the other hand, the oscillator of the present invention achieved the non-degraded pattern at approximately one hundred psi and the required droplet size was achieved at a several hundred psi.

The oscillator of the present invention can be made considerably shorter and with simpler manufacturing techniques. Specifically, in its preferred form, the oscillator has an interaction region length which is approximately four to eight times the power nozzle width, as compared to a minimum requirement of nineteen times the power nozzle width in prior art oscillators. In addition, an operable oscillator according to the present invention has been constructed with an aspect ratio (i.e. power nozzle depth to width) of 0.25, as compared to a minimum aspect ratio of one in the prior art.

Apart from improved liquid spray characteristics described herein, the improved fluidic oscillator, both in its preferred form and in variations thereof, is capable of advantageous operation with other operating fluids, such as gases, fluidized solid particles (i.e. tiny solid particles intermixed with fluid so as to be capable of fluid flow properties), etc. In addition, advantageous operation and results are obtained in both liquid and air ambient fluid environments.

A further advantage of the oscillator of the present invention relates to the fact that its frequency is linearly related to the rate of flow through the oscillator. As a consequence, the mechanical vibrations produced in the oscillator by deflecting jet may be sensed, without impeding flow, for purposes of monitoring the flow rate. In a particular embodiment, a vibratable reed is secured to the oscillator and arranged to vibrate at its resonant frequency which corresponds to a particularly desired flow rate.

BRIEF DESCRIPTION OF THE DRAWINGS

The above and still further objects, features and advantages of the present invention will become apparent upon consideration of the following detailed description of specific embodiments thereof, especially when taken in conjunction with the accompanying drawings, wherein:

FIGS. 9a and 9b are top and side plan views, respectively of a fluidic oscillator of the present invention modified to permit monitoring of rate of flow;

FIG. 10a is a view in perspective of a water brush employing the liquid spray concept in accordance with the present invention;

FIG. 10b is a view in section taken along line 10b—10b of FIG. 10a;

FIG. 11 is a diagrammatic view in perspective of a paint spray apparatus employing the liquid spray concepts of the present invention;

FIG. 12 is a diagrammatic plan view of an agricultural spray apparatus employing the liquid spray concepts of the present invention;

FIG. 13 is a side view in partial section of a liquid spray unit employing the concepts of the present invention;

FIG. 14 is a view in perspective of another spray unit employing the spray concepts of the present invention;

FIG. 15 is a plan view of an oscillator according to the present invention adapted to operate with a working fluid composed of fluidized solid particles;

FIG. 16 is a plan view of another embodiment of a fluidic oscillator according to the present invention, adapted to issue a fluid jet with which a second fluid or solid particles are mixed;

FIG. 17 is a plan view of a modified version of the embodiment of FIG. 16;

FIG. 18a is a partial view in perspective of the embodiment of FIG. 18;

FIG. 18b is a partial view in perspective of the embodiment of FIG. 16;

FIG. 19 is a view in perspective of a typical flow pattern issued from the embodiment of FIG. 16;

FIG. 20 is a view in perspective of a typical flow pattern issued from the embodiment of FIG. 17; and FIG. 21 is a plan view of another fluidic oscillator embodiment constructed in accordance with the present invention.

DESCRIPTION OF PREFERRED EMBODIMENTS

Figure 1:
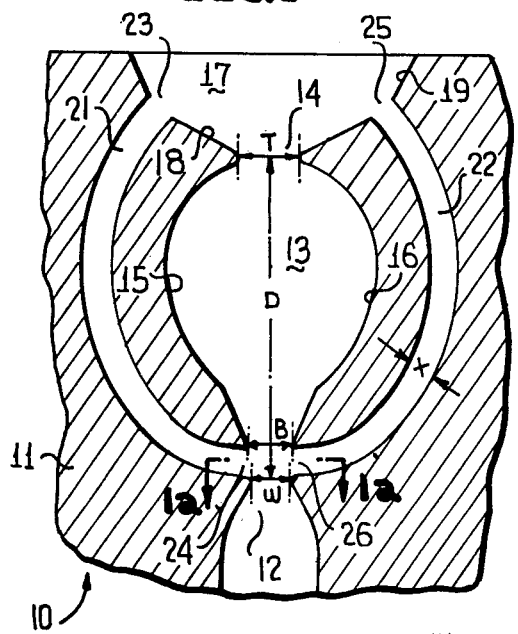
FIG. 1 is a plan view of a preferred embodiment of a fluidic oscillator configured in accordance with the present invention.

Referring specifically to FIG. 1 of the accompanying drawings, a fluidic oscillator 10 is illustrated in the form of various flow channels and passages. As is conventional in fluidics technology, the channels are preferably defined at one surface of a base plate 11, which surface is then sealed by a cover plate (not shown). Alternatively, plate 11 may be a center plate sandwiched between top and bottom cover plates. A tapered or convergent power nozzle 12 is adapted to receive pressurized fluid and issue a power jet of that fluid into the upstream end of an interaction region 13. The interaction region is defined between left and right sidewalls 15 and 16, respectively, which first diverge from power nozzle 12 and then converge toward an outlet throat 14 located at the downstream end of the region. Nozzle 12 and throat 14 are disposed in substantial alignment with one another along the longitudinal centerline of oscillator 10. An outlet region 17 is located immediately downstream of throat 14 and is defined between left and right outlet walls 18 and 19, respectively, which diverge in a downstream direction from throat 14. A left control passage 21 extends between outlet region 17 and the upstream end of interaction region 13 through port 23 defined in left outlet wall 18 and port 24 defined in left sidewall 15. A similar right control passage 22 extends between outlet region 17 and the upstream end of interaction region 13 through port 25 in right outlet wall 19 and port 26 defined in right sidewall 16. The upstream sides of ports 24 and 26 terminate at the outlet of power nozzle 12; the upstream sides of these ports are set back from the oscillator centerline relative to the upstream sides.

As is typical with fluidic oscillators, during operation of oscillator 10 a power jet of fluid issued from nozzle 12 is cyclically deflected between extreme positions defined by sidewalls 15 and 16. The phenomena producing oscillation is described subsequently; for the present, it should be noted that, when flowing along left sidewall 15, the jet is guided back to the right thereby and egresses through throat 14 in a direction generally toward right outlet wall 19. When flowing along right sidewall 16 the jet is guided back to the left thereby and egresses through throat 14 in a direction generally toward outlet wall 18. Intermediate the two extreme positions the jet sweeps across outlet region 17. Operation of this particular oscillator, in contradistinction to prior oscillators, is characterized by the fact that neither working fluid from the power jet nor ambient fluid is ingested back into interaction region 13 through control passages 21 and 22. Instead, when the jet flows along left sidewall 15 towards right outlet wall 19, it entrains and merges with outflow through right control passage 22; meanwhile, left control passage remains filled with fluid derived from the upstream end of interaction region 13.

Figure 1A:
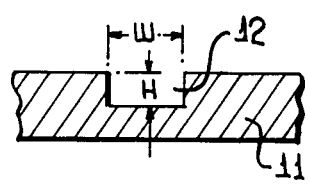
FIG. 1a is a view in section taken along line 1a—1a of FIG. 1.

The absence of inflow or ingestion from outlet region 17 is achieved by creating a static pressure at the upstream end of interaction region 13 which is higher than the static pressure in outlet region 17. This pressure difference is created by a combination of factors, including: the width T of throat 14 which is only slightly wider than power nozzle 12 so that the egressing power jet fully seals interaction region 13 from outlet region 17; and the length D of interaction region 13 from power nozzle 12 to throat 14, which length is significantly shorter than in prior art oscillators. It should be noted that the width X of control passages 21, 22 is smaller than the power nozzle. In referring to the widths T and X, it is assumed that the depth H (see FIG. 1a) of the various channels in the oscillator is constant throughout. If such is not the case, the cross-sectional areas of throat 14 and passges 21, 22 are to be considered. If all channels in oscillator 10 are of equal depth (i.e. into the plane of the drawing), and if the width of power nozzle 12 at its narrowest point is W, then the following relationships are suitable, although not necessarily exclusive, for operation in the manner described hereinbelow:

$T = 1.1W$ to $1.7W$ $D = 4W$ to $9W$

Considerable leeway in these dimensions exists for particular spray applications and depending to some extent upon other dimensions such as the setback B between the downstream ends of sidewalls 15 and 16, the transverse width of interaction region 13, and the width of openings 24, 26. On one of the specific successfully tested embodiments, $W = 1.1$ mm, $T = 1.35$ mm, $D = 7.3$ mm, $X = 0.65$ mm, $B = 1.4$ mm, the width of interaction region 13 at its maximum $= 4.32$ mm, openings 24, 26 $= 0.8$ mm, and the depth H of all channels was 0.5 mm. This unit was operated with water over an applied pressure range ($p$) from 1.0 to 160 psig and exhibited a frequency ($f$) in Hertz which followed the expression $f = 54.4 \sqrt{p}$; or $f = 1700 Q$ where Q is in gpm flow through the unit. The same oscillator, with air as a working fluid, had an operating frequency in Hertz approximately following the expression $f = 500 Q$. Substantially larger oscillators with similar relative dimensions and lower operating frequency ranges have also been constructed and successfully tested. For some applications it may be desirable to have different channel depths for various passages in the oscillator; under such circumstances the various widths, W, T and X would change accordingly to provide equivalent cross-sectional relationships.

Another interesting characteristic of this fluidic oscillator resides in the fact that it can be constructed with aspect ratios far smaller than possible with prior art fluidic elements. Aspect ratio is defined herein with the aid of FIG. 1a as the ratio of the depth H of the oscillator channels divided by the width W of the power nozzle 12. In the specific exemplary dimensions set forth above, it is noted that the ratio H/W is 0.5/1.1 or 0.45. In prior art oscillators, and in fluidic elements in general, it was considered that an aspect ratio of 1 was the lowest practical ratio. In fact, we have successfully tested an oscillator of the present invention having an aspect ratio of 0.25. The importance of this small aspect ratio resides in the fact that it permits simpler and less expensive fabrication techniques to be employed in defining the oscillator passages than was possible heretofore.

Figure 2:
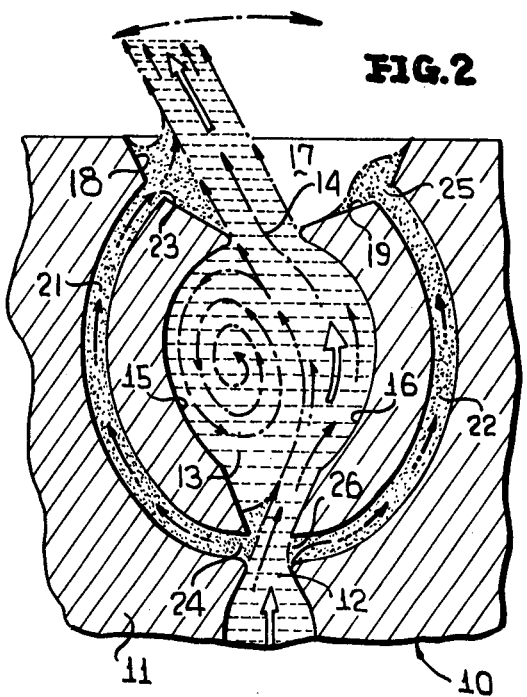
FIG. 2 is identical to FIG. 1 except for the inclusion of flow lines diagrammatically illustrating one operating mode of the oscillator.
Figure 3:
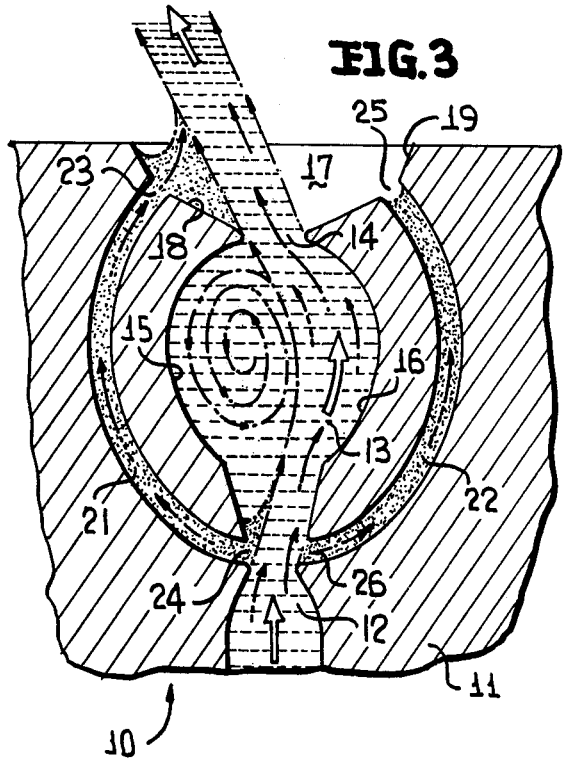
FIG. 3 is identical to FIG. 1 except for the inclusion of flow lines diagrammatically illustrating a second operating mode of the oscillator.

The absence of inflow to interaction region 13 during oscillator operation is particularly important for many liquid spray applications. For one thing, as best illustrated in FIGS. 2 and 3, as the liquid jet approaches the outlet wall, for example left outlet wall 18, it induces and merges with liquid outflow from left control passage 21. This merger of power jet liquid with control liquid prevents the power jet from impinging directly against outlet wall 18; that is, the outflow from the control passages 21, 22 provides a sort of cushioning effect for the deflecting jet. Consequently, the edges of the jet do not experience the shearing effect which would result from its impinging against the outlet wall. Minimization of the shearing effect in turn minimizes the formation of extremely small or fine droplets at the stream boundary and enhances the overall uniformity of size of the droplets formed from the sweeping jet. In addition, outflow through control passages 21, 22 ensures against ingestion of jet liquid or ambient fluid into the interaction region. In most prior art fluidic oscillators, the very operation of the oscillator depends upon inflow of jet or ambient fluid to the interaction region via such control or feedback passages. Such inflow is undesirable in many spray applications. Oscillator 10, on the other hand, eliminates this problem.

The operation of oscillator 10 may be described as follows, with reference to FIG. 2. Assume initially that liquid under pressure is applied to power nozzle 12 and that the oscillator is located in an ambient air environment. The liquid jet which is issued by power nozzle 12 is initially directed straight through interaction region 13 and egresses through throat 14. The narrowness of throat 14 results in portions of the jet periphery being scooped off and recirculated along sidewalls 15 and 16 to form vortices on the sides of the jet in the interaction region. Due to slight perturbations in the jet, the vortex on one side becomes stronger than that on the other and therefore tends to deflect the jet to flow along one of the sidewalls (e.g. right sidewall 16 as illustrated in FIG. 2). The remaining vortex further increases the pressure in interaction region 13 which is effectively sealed from outlet region 17 by the egressing power jet. The liquid fills the interaction region and the static pressure therein builds up to a higher level than that in outlet region 17, whereupon liquid begins to flow from the interaction region into control passages 21, 22. Meanwhile, the power jet is directed by right sidewall 16 to flow generally toward left outlet wall 18. Liquid outflow through left control passage 21 is aided by jet aspiration and merges with the jet at left outlet wall 18, preventing the jet from impinging against the wall itself. This is illustrated clearly in FIG. 2 wherein the large arrows represent the flow of the liquid jet and the smaller arrows represent control passage outflow. The jet tends to increase the flow rate of liquid through control passage 21 when in the position shown in FIG. 2 because of the aspiration effect the jet has on the left control passage as it flows along left outlet wall 18. This aspiration tends to reduce the pressure in left control passage 21 relative to that in right control passage 22 which is filled with liquid and in which no similar aspiration occurs at this time. The pressure differential in the control passages is reflected at the upstream end of the interaction region and causes the jet to be deflected across the interaction region so as to flow along left sidewall 15 and toward right outlet wall 19. During such deflection the jet sweeps from left to right across the outlet region 17. Upon approaching right outlet wall 18 the jet begins to aspirate liquid from right control passage 22 and ceases aspiration through left control passage 21. The pressure on the right side of the power stream is therefore rendered lower than on the left side and the jet is deflected once again. This cyclic deflection of the jet results in a cyclic sweeping back and forth of the jet across outlet region 17.

We have found that the flow conditions in the unaspirated control passage (e.g. - right control passage 22 when the jet is directed along left outlet wall 18; left control passage 21 when the jet is directed along right outlet wall 19) are dependent upon the pressure of the liquid applied to power nozzle 12. Specifically, for low and intermediate pressures the liquid in the unaspirated passage tends to form a convex meniscus which bulges outwardly from opening 25 or 23 into the outlet region as illustrated in FIG. 2 for opening 25. At high applied pressures the meniscus becomes concave, as illustrated in FIG. 3 for opening 25. In all cases, however, the unaspirated passage remains full of liquid and prevents any flow back into interaction region 13. Therefore, over an entire cycle, there is a net flow outwardly (i.e. to the outlet region) from both control passages 21, 22.

The relative shortness of interaction region 13 (i.e. dimension D) is particularly interesting in view of the fact that the prior art indicates that short interaction regions render the power jet incapable of oscillation or even significant deflection. The power jet in the present invention not only oscillate within a short interaction region, but does so as a frequency which varies in direct proportion to the flow rate through the oscillator. This latter feature is discussed subsequently herein.

The build-up of a higher pressure at the upstream end of interaction region 13 relative to outlet region 17 is likewise antithetical to the teachings regarding prior art fluidic oscillators. Specifically, most prior art oscillators require feedback flow toward the interaction region to achieve deflection of the power jet; such feedback flow requires a low pressure at the upstream end of the interaction region. Moreover, too high a pressure in the interaction region has heretofore been thought to impede jet deflection. In the present invention, however, high frequency oscillation readily occurs. In addition, it is this pressure build up which causes flow to be directed outward through the control passages, a crucial aspect of oscillator 10.

Figure 4:
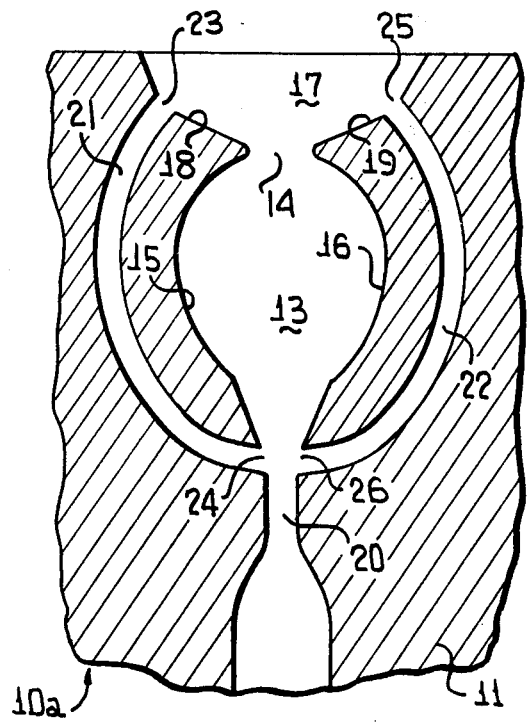
FIG. 4 is a plan view of an alternative embodiment of a fluidic oscillator configured in accordance with the present invention.

Referring to FIG. 4, another embodiment 10a of the oscillator of the present invention includes a parallel-wall power nozzle 20 as contrasted to the converging or tapered power nozzle 12 of oscillator 10. In all other respects the two oscillators are the same and like parts are designated with the same reference numerals in each. The relative dimensions between W and D, T and X change somewhat in oscillator 10a because of the power nozzle configuration. Specifically, in the tapered or converging nozzle 12 of FIG. 1 the cross-section of the jet at a distance approximately W/2 downstream of the nozzle is somewhat smaller than the nozzle-cross-section. This contraction of the jet is the well-known vena contracts phenomenon. In parallel-wall nozzle 20, however, the vena contracta effect is negligible. Consequently, if nozzles 20 and 12 are of the same width, convergent nozzle 12 issues a narrower jet than does parallel-wall nozzle 20. Therefore, the preferred range of relative dimensions between W' and D, T and X in oscillator 10' change accordingly. The important point is that the dimensions are selected in order that, during operation, the static pressure at the upstream end of interaction region 13 is positive relative to the static pressure in outlet region 17 so that no fluid is ingested into the interaction region through the control passages.

Figure 5:
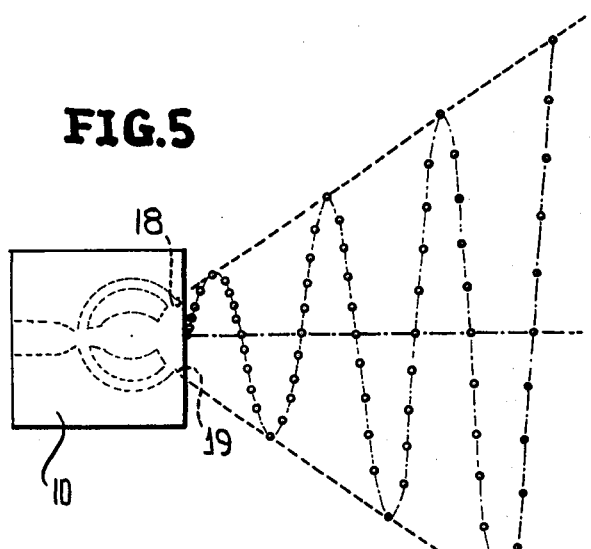
FIG. 5 is a diagrammatic illustration of a spray pattern issued during one operating mode of a fluidic oscillator constructed in accordance with the present invention.
Figure 6:
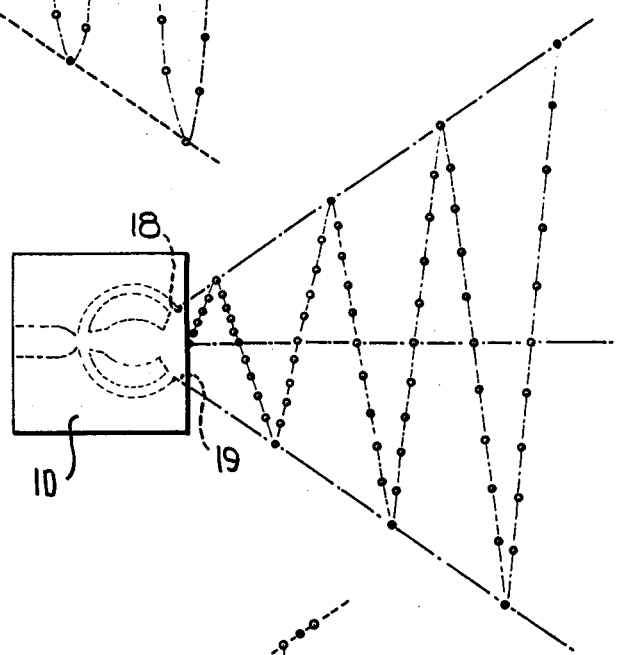
FIG. 6 is a diagrammatic illustration of a spray pattern issued during another operating mode of a fluidic oscillator constructed in accordance with the present invention.
Figure 7:
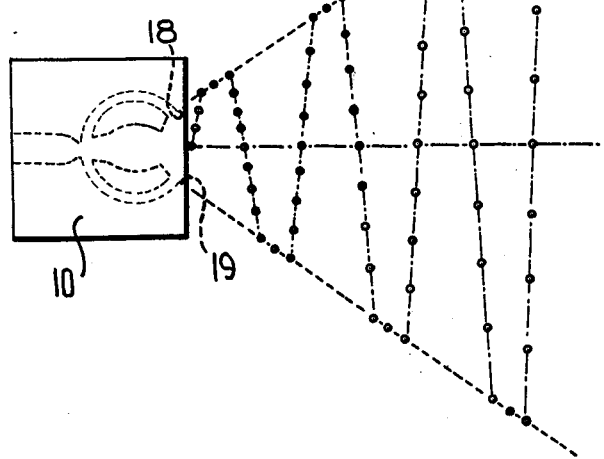
FIG. 7 is a diagrammatic illustration of a spray pattern issued during still another operating mode of a fluidic oscillator constructed in accordance with the present invention.

Depending upon the dimensions of the various parts of the oscillator, it is capable of delivering a variety of liquid spray patterns. Specifically, as the power jet sweeps back and forth it breaks up into droplets of generally uniform size, which size depends upon a number of factors including the size of the oscillator, frequency of oscillation, etc. These droplets are distributed in a spray pattern having a more or less fan configuration, the sides of which are defined by the angle between the outlet walls 18, 19 of the oscillator. Distribution of the droplets within the spray pattern depends upon the oscillator dimensions, primarily on the width T of throat 14. Referring to FIG. 5, a liquid spray pattern is illustrated in which the droplets are distributed in a sinusoidal pattern, one cycle for each cycle of the jet in the oscillator. In FIG. 6 there is illustrated a triangular pattern, while FIG. 7 illustrates a more or less trapezoidal pattern. In each case the overall pattern has the same size fan-shape, assuming of course that outlet walls 18, 19 subtend the same angle in each case. The difference resides in the distribution of droplets within that fan and depends upon the behavior of the sweeping jet in oscillator 10. Specifically, the triangular pattern of FIG. 6 results from a sweeping action of the jet whereby it has negligible dwell at the extreme positions of its sweep and exhibits virtually no change in deflection speed while changing direction. This mode of operation is produced when the width of throat 14 is in the narrowest part of its range. The sinusoidal pattern of FIG. 5 is produced from a sweeping action of the jet whereby it has minimal dwell at the extreme sweep positions but slows down upon approaching each extreme position. This mode of operation results from the width of throat 14 being in an intermediate portion of its permissible range. The trapezoidal pattern of FIG. 7 results from the jet experiencing considerable dwell at the extreme sweep positions; that is, the jet remains stationary for a finite interval upon reaching each extreme position. This mode of operation is effected when the width of throat 14 is at the wider end of its range. In one example, for otherwise identical oscillators, varying only the width T of throat 14: the triangular pattern of FIG. 6 was achieved with T = 1.2W, the sinusoidal pattern of FIG. 5 was achieved with T = 1.3W; the trapezoidal pattern of FIG. 7 was achieved with T =

1.7W, which is at the extremity of desired range for oscillator 10.

The triangular pattern of FIG. 6 provides the most uniform distribution of droplets within the fan configuration. This is evident because the jet sweep speed is constant throughout the entire cycle. The sinusoidal pattern is less uniform with respect to droplet distribution because of the slow down of the jet near the sweep extremities. The trapezoidal pattern has the least uniform distribution of droplets, with a considerably disproportionate amount of liquid being distributed near the pattern boundaries. In fact, the trapezoid pattern tends to appear as defined slugs of liquid following the boundary lines of the fan configuration. This pattern is not desirable for liquid spray applications of the type with which the present invention is concerned. Rather, it is the patterns having uniform or nearly uniform droplet distribution to which the invention is directed.

As mentioned previously, oscillator 10 is particularly suited for use in paint spraying. A paint spraying apparatus employing two such oscillators is illustrated in FIG. 11 to which specific reference is now made. Oscillators 30 and 31, both constructed in accordance with the requirements set forth above for oscillator 10, 10a, etc., are mounted on a bracket member 32. The oscillators are oriented such that the planes of their power jet deflection (i.e. the planes of the issued fan-shaped spray patterns) are substantially co-planar. Bracket 32 is smoothly translatable in a direction perpendicular to the spray pattern planes by suitable drive means, designated schematically by block 33. Liquid paint is supplied under pressure to both oscillators 30, 31 through tubing 34. The entire apparatus is positioned to permit the issued spray patterns to be directed against a surface 35 which is to be painted. In the particular arrangement illustrated, surface 35 is perpendicular to the planes of the issued spray patterns. The oscillators 30, 31 are arranged such that their patterns strike surface 35 immediately adjacent one another; in this manner, if each spray pattern contains uniformly distributed paint droplets, the two patterns together provide two painted stripes of uniform paint content as drive means 33 translates the two oscillators in a direction parallel to painted surface 35. It should be noted that each oscillator could be separately supplied with paint, for example, paints of different colors, so that two different colored stripes can be painted onto surface 35. Likewise, any number of oscillators, oriented in any manner, can be employed within the same inventive concept.

The significant feature of the apparatus of FIG. 11 resides in the fact that the issued spray patterns are produced at pressures which are at least an order of magnitude (i.e. factor of ten) lower than the pressures required to provide the same pattern with a shear nozzle. By properly selecting the oscillator size and operating frequency, the desired droplet size can be effected for efficient paint spraying. Importantly, the droplet size is uniform throughout the spray pattern, thereby avoiding the formation of globules which yield uneven painting. In addition, the desired droplet distribution pattern (reference FIGS. 5 and 6) may be chosen to effect the desired thickness of applied paint at different portions of the painted stripe.

The technique illustrated in FIG. 11 is also adaptable to electrostatic spraying wherein the paint is charged to one polarity and the target (i.e., surface 35) is charged to the opposite polarity. The benefit of this arrangement, as is well known, is that the paint is electrostatically attracted to the surface so that very little paint misses the intended target. This electrostatic approach, combined with the paint delivery efficiency afforded by the uniform droplet size of the oscillator, further enhances the overall efficiency of the apparatus. With or without the electrostatic arrangement, however, the main advantage of the apparatus of FIG. 11 resides in its ability to provide the desired spray pattern and sufficiently small droplets at pressures which are far lower than previously required in the prior art.

Similar advantages accrue to the use of oscillator 10 in an agricultural spray apparatus, such as the apparatus illustrated in FIG. 12. Referring to FIG. 12, an agricultural spray apparatus includes a motorized vehicle such as truck 40 adapted to hold a volume of liquid such as fertilizer, pesticide, etc., to be sprayed onto a row of crops 41. A pump 42 carried by the truck 40 is adapted to force the liquid through conduits 43 extending from each side of the truck and terminating in respective manifolds 44. Secured in manifolds 44 so as to receive pressurized liquid are respective rows of oscillators (not visible in FIG. 12) of the type described in relation to FIG. 1, etc., The oscillators are arranged to issue their fan-shaped spray patterns one adjacent the other so as to provide full and uniform converage of crops 41 with the sprayed liquid, as diagrammatically indicated by the dashed lines in FIG. 12.

As is the case for paint spraying, the oscillators of the present invention are able to provide the desired agricultural spray pattern at far lower liquid pressures than required in prior art agricultural sprayers. Moreover, the oscillator of FIG. 1 provides such spray without introducing smaller than desirable droplet sizes. Specifically, as indicated previously, it is a requirement for many agricultural spray applications that droplet sizes be no smaller than approximately 80 microns. The oscillator of FIG. 1 can be constructed sufficiently large to produce droplets sufficiently large to meet these requirements. Moreover, unlike prior art fluidic oscillators, the oscillator of FIG. 1 avoids shearing of the power jet against the outlet walls by merging control flow with the jet. By avoiding the shearing effect the oscillator avoids the unintended production of tiny droplets, or "fines", which are smaller than agricultural spray requirements.

An interesting characteristic of the oscillator of FIG. 1 is the fact that its frequency is linearly related to the rate of flow through the oscillator over an extremely wide range of flow rates. The oscillator described in U.S. Pat. No. 3,563,462, for example, exhibits a generally parabolic frequency versus flow characteristics. The linear characteristic of the present invention permits the frequency to be measured and read directly on a flow rate scale. Importantly, the frequency can be measured without tapping off or otherwise impeding the flow which can therefore be delivered in its entirety for its intended purpose. Referring specifically to FIGS. 9a and 9b of the accompanying drawings, a flow meter 50 includes an inlet passage 51 feeding an oscillator 52 of the same general type as described herein in reference to FIG. 1, etc. Oscillator 52 delivers its sweeping jet into the relatively wide upstream end of a measurement chamber 53 which tapers in a downstream direction to feed an outlet passage 54. The flow meter 50 is formed in two abutting surfaces of respective plates 55, 56, with passages 51 and 54 and chamber 53 formed partially in both surfaces. Oscillator 52 is formed in plate 56 only, although this is not a necessary requirement and depends in part on the size oscillator to be employed.

A piezoelectric transducer 57 is located in a suitably provided hole defined through plate 55 at chamber 53. Transducer 57 includes a pair of leads 58 which are adapted to be connected to an electrical frequency-measuring apparatus. As is well known, a piezoelectric transducer is responsive to mechanical displacement in one or more surfaces thereof to provide an electrical signal having amplitude and frequency proportional to the mechanical displacement.

In operation, pressurized fluid applied to inlet passage 51 causes oscillator 52 to provide a sweeping fluid jet in the manner described herein with reference to FIG. 1, etc. The swept jet is directed into chamber 53 in which it alternately strikes opposing chamber sidewalls and is directed through outlet passage 54 to a utilization device. The sweeping jet produces vibrations in the flow meter body, particularly in the measurement chamber 53 wherein the jet alternately impinges against the chamber sidewalls. These vibrations are sensed by transducer 57 which develops an electrical signal at twice the frequency of the jet, across leads 58. The electrical signal is at twice the jet frequency because the transducer is incapable of discerning between half cycles of the jet; that is, impingement of the jet against each sidewall in chamber 53 appears the same to the transducer. Since, as mentioned previously, the jet frequency is linearly related to flow rate through the oscillator over a wide range of flow rates, the frequency of the electrical signal may be applied directly to a conventional frequency meter having a scale calibrated in flow units.

A major advantage of the flow measuring arrangement in FIGS. 9a and 9b resides in the fact that none of the fluid need be tapped-off nor impeded for the purpose of measuring flow. This particular embodiment is designed to be inserted in any flow line through which it is desired to measure flow rate. It should also be noted that this embodiment could be modified to do away with chamber 53 and passage 54 for spray applications such as those described with reference to FIGS. 11 and 12. Under such circumstances the transducer would be positioned on the oscillator itself to sense the frequency of vibrations in the oscillator body. The advantage of such an arrangement is that the frequency is sensed at the spray-producing member (i.e. the oscillator) and no spray-collecting chamber, such as chamber 53, is required as in the non-spray application.

Figure 8A:
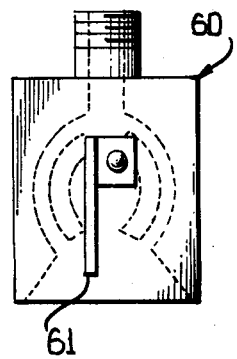
FIGS. 8a and 8b are top and side plan views, respectively, of a fluidic oscillator of the present invention modified to permit sensing of a particular flow rate.
Figure 8B:
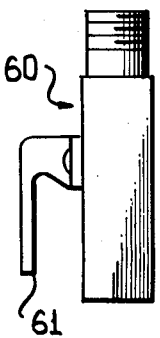

For many spray applications it is desirable that a specific flow rate, and only that flow rate, be attained for proper spray delivery. Under such conditions the embodiment illustrated in FIGS. 8a and 8b is advantageous. Referring specifically to FIGS. 8a and 8b, an oscillator 60, of the type described in relation to FIG. 1, etc., has a vibratable reed 61 or similar vibrating member secured thereto. Reed 61 is chosen to have a resonant frequency corresponding to twice the oscillator frequency produced by the desired flow rate through the oscillator. When this flow rate is achieved, the vibrations in oscillator 60 cause reed 61 to vibrate, serving as an indication that proper operating conditions exist. The reed does not vibrate at other frequencies.

Of course a reed 61 is a simple example of a resonant member which can serve to indicate that the desired flow rate exists. Other possibilities include: a tuning fork to provide an audible indication; a magnetic resonant reed, the vibration of which is sensed by a magnetic pick up arrangement and transduced to provide an electric indication, etc. In each case, no flow sampling or impeding is necessary, yet an accurate flow rate indication is provided.

Apart from commercial and/or industrial spray applications discussed thus far herein, the oscillator of the present invention has numerous applications in the consumer product field. One such application is an oral irrigator as described and claimed in U.S. Pat. No. 3,973,558. filed on concurrent date herewith by R. Stouffer and P. Bauer and entitled "Swept Jet Oral Irrigator". Another such application is illustrated in FIGS. 10a and 10b to which specific reference is now made. A water brush 70 includes a body member 71 having an inlet tube at its inlet end adapted to receive water under pressure from a faucet or other plumbing installation. Within body member 71 is an oscillator (not shown) of the type described in relation to FIG. 1, etc. The oscillator delivers its sweeping jet through a generally rectangular outlet opening 72 defined at its outlet end, it being understood that the outlet opening configuration can be varied in accordance with the desired spray pattern. Surrounding outlet opening 72 at the outlet end of the brush is a generally teardrop-shaped wall 73 of open cell foam material. This material is pervious to air and of soft texture, much like a sponge. The teardrop configuration is oriented with its longest dimension co-planar with the plane of the spray issued from outlet opening 72.

Water brush 70 is intended to be used by brushing the downstream end of wall 73 along the user's body as a sweeping water jet issues against the body from within the wall. The high frequency sweeping action of the water jet acts to loosen dirt particles. Wall 73 serves as a splash guard and is flexible, soft, and porous to air. If this were not the case, the sweeping jet might tend to attach to inner surface of wall 73 due to Coanda effect. Entry of air into the region enclosed by wall 73 prevents such attachment.

The water brush may be used at a sink for the efficient removal of make-up and other greasy matter from the face and hands of the user. In addition the water brush may be used in the shower to remove stubborn dirt and grease from other parts of the body. In some instances a pre-coating of the body part to be cleaned with soap or the like facilitates the cleansing action of the water brush.

In addition to its cleansing effect, the water brush is sensually pleasing to the user, providing a tingling effect on the skin as the jet sweeps back and forth at high frequency. The individual droplets, successively striking the skin at adjacent locations, provide a positive massaging action by depressing the skin tissue at the point of impact and forcing the adjacent tissue, including that depressed by the preceding droplet, outward. The action does not, therefore, depend upon the natural resilience or elasticity of the skin tissue to provide a massaging and blood circulating effect; rather it positively forces the depressed tissue back to its natural shape. This permits the sweeping jet massage to be effected at higher frequencies than are possible with simple repetitive pulsing jets because the useful frequency of a pulsed jet is limited by the time required for the skin to rebound from a depression by its own elasticity.

Other personal spray apparatus may be designed to take advantage of the improved low-pressure spray characteristics of the oscillator described herein. Referring specifically to FIG. 13, a personal atomizer 80 takes the form of a liquid container 81 having a removable cap 82. A conventional flexible pressure bulb 83 is capable, when squeezed, of delivering air under pressure into container 81 through a short tube 84 extending through cap 82 and terminating proximate the top of the container. Liquid outflow from container 81 is via a longer tube 85, having its inlet end disposed proximate the bottom of the container, extending through cap 82 and terminating at the inlet of a fluidic oscillator 86 of the type described in relation to FIG. 1, etc.

The pressure bulb 83 drives liquid under pressure up through tube 85 in a conventional manner. Upon reaching oscillator 86 the pressurized liquid forms a sweeping jet in the manner described herein, to in turn provide the desired spray pattern of liquid droplets.

The apparatus of FIG. 13 has utilization as an applicator for perfumes, colognes, deodorants, etc. In addition, it may be used for such applications as paint touchups, solvent applicators, etc. Further, the apparatus may be used to deliver a sweeping jet of gas or other non-liquid fluid. It should also be noted that all of these applications of the oscillator are suitable for use with other pressure sources than bulb 83, including, but not limited to, aerosol cans, etc.

Referring to FIG. 14, another personal applicator 90 includes a flexible fluid container 91 which may itself merely be squeezed to effect the necessary pressure to create the desired spray. A cap 92 for the container has an oscillator 93 constructed integrally therewith and a flexible tube 94 secured thereto so as to extend into container 91. The remote or inlet end of tube 94 has a weight 95 attached thereto to assure that the inlet end of tube 94 is always disposed at or near the lower-most portion of the container interior, regardless of the orientation of the container.

Flexible tube 94 serves to supply pressurized fluid to oscillator 93 when container 91 is squeezed. Apparatus 90 can be utilized in the same applications as apparatus 80 but but has a distinct advantage over that apparatus. Specifically, apparatus 90 may be held in any orientation, including upside down, and still deliver fluid spray when squeezed. This is due to the fact that weight 95 tends to maintain the inlet end of tube 94 submerged for any orientation of the container.

In the case of both apparatus 80 and 90, the containers may be disposable and/or marketed separately from the cap and oscillator structure which can be re-used with other containers.

As briefly suggested hereinabove, the oscillator of the present invention may be employed with working fluids other than liquid. For example, the working fluid may be fluidized solid particles which are tiny particles entrained in air or other gas such that the mixture takes on the flow characteristics of a gas or liquid. Typical examples are de-hydrated solids such as dried paint and milk, granulated solids such as sugar, powdered material such as gun powder, etc. In many instances it is possible to deliver the fluidized solid to an unmodified oscillator, such as that illustrated in FIG. 1. In some case, however, the solid particles tend to fall out of the fluidized mixture within the oscillator interaction region. To prevent this possibility the modified oscillator illustrated in FIG. 15 may be employed. Specifically, oscillator 100 includes the same components as oscillator 10, which components are designated by the same reference numerals as in FIG. 1. In addition, oscillator 100 includes an air inlet pipe 101 which feeds manifold 102. The manifold, in turn, distributes air through both sidewalls 15, 16 of interaction region 13 via a plurality of ports 103. The purpose of inlet pipe 101, manifold 102, and ports 103 is to supply air or other gas under pressure form a source (not shown) to both sides of the interaction region to increase the pressure thereat. The increased pressure prevents any solid particles which may fall out of the mixture from collecting in and clogging interaction region 13. Instead, the particles are forced to egress through throat 14 along with the egressing jet of fluidized particles.

The jet of fluidized solid particles egressing from oscillator 100 takes the form of a cloud of sinusoidal or triangular wave shape as illustrated in FIG. 19. In this form the particles may either be sprayed onto a surface (as in the case of paint) or distributed as desired according to the particular process. Another form of the oscillator for delivering the pattern of FIG. 19 is illustrated in FIGS. 16 and 18. Specifically, oscillator 105 contains the same components as oscillator 10 but additionally includes a tube 106 extending through plate 11 and terminating generally in the region of throat 14. The termination of tube 106 is so positioned that the jet egressing from throat 14 always passes over that termination, irrespective of the jet position. Tube 106 is employed to introduce solid particles or fluid material into the sweeping jet as it egresses through throat 14. The introduced matter may either be aspirated through tube 106 by the jet or it may be forcefully injected thereinto under pressure. In either case, the jet carries the introduced material from the oscillator in a pattern such as that illustrated in FIG. 19. Typically, the working fluid may be air and the material introduced via tube 106 may be a particulated solid. Alternatively, the working fluid may be any liquid, gas or fluidized solid, and the material introduced thereinto via tube 106 may also be liquid, gas, or particulated solid. Tube 106, for example, may be employed in conjunction with water brush 70 of FIGS. 10a, 10b to introduce soap or the like into the issued water jet; or tube 106 may be employed in conjunction with the agricultural spray apparatus of FIG. 12 to introduce pesticide material into a fertilizer spray, or vice versa; etc.

In some instances it may be desirable to introduce material to the issued spray so that the introduced material is not distributed over the entire spray pattern. For example, FIG. 20 illustrates a spray pattern comprising a series of clouds of fluidized solid particles, directed along a generally straight line. An oscillator modification for producing such a pattern is illustrated in FIGS. 17 and 18a. Specifically, oscillator 110 is similar to oscillator 10 and includes components designated by similar reference numerals. In addition, oscillator 110 includes a tube 111, similar to tube 106 of oscillator 105 except that tube 111 communicates with outlet region 17 considerably downstream of throat 14. In this position, the termination of tube 111 is passed by the sweeping jet only twice during each sweep cycle; that is, the jet passes over the tube 111 only at or proximate the midpoint of its sweep but not at or near the extreme sweep positions. Of course tube 111 may be positioned so as to only be passed by the jet proximate an extreme position; or more than one such tube may be provided so that a plurality of angularly related patterns, such as the one illustrated in FIG. 20, are provided. In any case, the fluid pattern issued from oscillator 110 contains matter introduced by tube 111 only in discrete portions of the pattern. The types of fluids and materials which can be employed with oscillator 110 are the same as those mentioned for oscillator 105.

Another embodiment of the oscillator of the present invention is illustrated in FIG. 21. Specifically, oscillator 120 includes the same components, similarly numbered, as oscillator 10, except for the power nozzle. Instead of being tapered line power nozzle 12, power nozzle 121 of oscillator 120 is configured as a sharp-edged orifice, similar to the power nozzle orifice described in U.S. Pat. No. 3,608,703 to Bahrton. As described in that patent, a jet issued from a sharp-edged orifice is more sensitive to deflecting forces and therefore permits a shorter interaction region to be employed. The use of power nozzle 121 therefore permits the oscillator to be constructed in an even shorter version than oscillator 10. Importantly, however, the outlet throat 14 and conrtrol passages 21, 22 must be sufficiently narrow to assure that the static pressure at the upstream end of the interaction region 13 is positive relative to the outlet region 17 pressure during operation. This, as previously described, assures that fluid flows outwardly from interaction region 13 to outlet region 17 through control passages 21, 22. This outflow, in turn, prevents ingestion of matter into the interaction region and prevents the issued jet from impinging upon the outlet walls where it would be sheared to produce undesirably tiny droplets.

In summary, the main advantages of the fluidic oscillator of the present invention and as described herein are as follows:

(a) Liquid spray may be achieved in a desired pattern at lower pressures than required in the prior art.

(b) Uniform droplet size may be achieved if desired; in any case, minimum and maximum droplet sizes may be readily achieved at lower pressures than required in the prior art.

(c) No fluid is ingested into the interaction region from the outlet region.

(d) Flow rate through the oscillator may be simply measured without diverting the fluid.

(e) The oscillator can be constructed in a much smaller size than possible for prior art oscillators of the type having flow-reversing interaction region sidewalls.

(f) The oscillator can be constructed with shallower channels than prior art fluidic elements; that is the aspect ratio (power nozzle depth to power nozzle width) is smaller. This permits simpler and less expensive manufacturing process to be employed.

With respect to the advantage of small aspect ratio, it should be noted that the smaller ratio has no effect on the operating frequency of the oscillator. In other words, all other dimensions remaining the same, changing the channel depth does not change the operating frequency at any operating pressure. Further, this advantage should not be considered limiting the aspect ratio; that is, large aspect ratios work equally as well.

It should be noted that the sinusoidal pattern of FIG. 5 tends to contain droplets of more uniform size than the triangular pattern of FIG. 6, although the droplet size variation in the pattern of FIG. 6 is by no means large. As mentioned, the triangular pattern of FIG. 6 provides more uniform spatial distribution of liquid than the sinusoidal pattern of FIG. 5, although the sinusoidal distribution is acceptable for most spray applications. The optimum combination of droplet size uniformity and distribution uniformity is obtained by compromise between the two patterns.

Another advantage of the present invention resides in the fact that the oscillator does not continuously drip when not operating, a problem which exists with shear nozzle liquid sprayers.

Still another advantage of the fluidic oscillator of the present invention resides in the fact that it operates both in liquid and gas environments with either liquid or gas working fluid. Most fluidic oscillators in the prior art do not operate in all ambient environments.

The oscillator described herein is capable of delivering more viscous fluid in a non-degraded spray pattern at a given fluid pressure than is possible in the prior art. This is particularly advantageous in aerosol sprays wherein the available pressure is pretty much limited. In addition, some aerosol sprays include solvent in the delivered fluid to reduce viscosity and thereby lower the viscosity sufficiently to permit development of a spray pattern. The present oscillator permits a significant reduction in the amount of solvent required in such spray units. Reduction of solvent, in turn, reduces "fines" or tiny particles which would otherwise be produced by the interaction of ambient air with the less viscous fluid. Moreover, reduction of solvent reduces the tendency of the sprayed fluid (e.g. paint) to run after striking the target surface.

Still another advantage of the present oscillator relates to the sweeping pulsation effect it produces. It has been shown that pulsating, as opposed to steady, flow provides improved results for skin de-germing and wound lavage. The present oscillator permits such pulsation at high frequencies and low pressures without stinging the patient. In fact, the tingling feeling felt by the patient tends to numb the local area rather than sting.

The oscillator as described thus far is designed to produce a generally planar fan-shaped spray pattern. This may be modified by changing the configuration of the outlet walls. In addition, the spray pattern may be made other than planar by appropriately configuring the oscillator so that plate 11 is not planar. For example, if plate 11 were semi-cylindrical so that deflecting jet is forced to deflect across a semi-cylindrical surface, the issued spray would not be flat but in the form of a conical or semi-cylindrical sheet of liquid. Other configurations would produce similar spray pattern contours.

A partial list of possible applications for the fluidic oscillator of the present invention follows:

(1) agricultural spray
(2) paint spray
(3) oral irrigator
(4) aerosol sprays
(5) fluidized solid processing
(6) flow metering
(7) atomization
(8) fluid mixing
(9) burner fuel injection
(10) fiber laying
(11) drying
(12) massaging
(13) cleansing With respect to cleansing it should be noted that the sweeping jet is efficient for cleaning surfaces of all types. In addition, it has advantageous utility in the field of wound lavage wherein liquid sprays of water and/or antiseptic solution, sprayed on a wound, a provide efficient sterilization.

In its broadest terms, the present invention provide a low pressure liquid spray method and apparatus in which a liquid jet is cyclically deflected to provide a controlled spray pattern with controlled droplet size and controlled liquid distribution. In a narrower sense, the specific oscillator described herein constitutes air inventive embodiment of the broader invention.

While we have described and illustrated specific embodiments of our invention, it will be clear that variations of the details of construction which are specifically illustrated and described may be resorted to without departing from the true spirit and scope of the invention as defined in the appended claims.

We claim:

1. A personal spray device characterized by a nozzle which issues a liquid jet which is swept in at least one dimension transverse to the nominal jet flow direction, causing said jet to break up into liquid droplets, said device comprising:

a body member;

an inlet means defined in said body member for receiving liquid under pressure;

means for establishing a liquid pressure inside said body member which is greater than ambient pressure;

jet-defining means within said body member responsive to the received liquid for forming said liquid jet;

an outlet opening defined in said body member for issuing said jet exteriorly of said body member, said outlet opening being elongated in at least said one dimension transverse to the flow direction of said jet therethrough;

jet-sweeping means operated solely by the pressure of said liquid and located within said body member for repetitively sweeping said jet in at least said one dimension; and a guard member projecting from said body member and disposed about said outlet opening.

2. The device according to claim 1 wherein said guard member is a wall of cellular foam material.

3. The device according to claim 2 wherein said wall has a teardrop-shape cross-section taken transverse to the direction of flow.

4. The device according to claim 1 wherein said jet-sweeping means is a fluid oscillator having no moving parts.

5. The apparatus according to claim 1 wherein said guard member is made of soft, flexible material which is porous to air.

* * * * *